(12) United States Patent
Nakayama et al.

(10) Patent No.: US 9,567,284 B2
(45) Date of Patent: *Feb. 14, 2017

(54) HEXAESTER OF MONO-FORMAL BIS PENTAERYTHRITOL

(71) Applicant: KH Neochem Co., Ltd., Chuo-ku, Tokyo (JP)

(72) Inventors: Shingo Nakayama, Tokyo (JP); Takuya Nishimura, Mie (JP); Toshihiro Inayama, Mie (JP)

(73) Assignee: KH NEOCHEM CO., LTD., Tokyo (JP)

( * ) Notice: Subject to any disclaimer, the term of this patent is extended or adjusted under 35 U.S.C. 154(b) by 54 days.

This patent is subject to a terminal disclaimer.

(21) Appl. No.: 14/438,057

(22) PCT Filed: Oct. 22, 2013

(86) PCT No.: PCT/JP2013/078513
§ 371 (c)(1),
(2) Date: Apr. 23, 2015

(87) PCT Pub. No.: WO2014/065250
PCT Pub. Date: May 1, 2014

(65) Prior Publication Data
US 2016/0311751 A1    Oct. 27, 2016

(30) Foreign Application Priority Data
Oct. 24, 2012 (JP) ................................ 2012-234840

(51) Int. Cl.
*C07C 55/24* (2006.01)
*C07C 59/305* (2006.01)
(Continued)

(52) U.S. Cl.
CPC ............ *C07C 59/305* (2013.01); *C09K 5/045* (2013.01); *C10M 105/38* (2013.01);
(Continued)

(58) Field of Classification Search
CPC ................................. C07C 55/24; C07C 69/33
See application file for complete search history.

(56) References Cited

U.S. PATENT DOCUMENTS 2,464,430 A    3/1949    Barth et al.
4,883,902 A *  11/1989   Gohbayashi .......... C07C 69/732
                                                      560/75
(Continued)

FOREIGN PATENT DOCUMENTS

JP    53-88825 A    8/1978
JP    04-072390 A   3/1992
(Continued)

OTHER PUBLICATIONS

International Search Report (PCT/ISA/210) mailed on Dec. 24, 2013, by the Japanese Patent Office as the International Searching Authority for International Application No. PCT/JP2013/078513.
(Continued)

*Primary Examiner* — John Hardee
(74) *Attorney, Agent, or Firm* — Buchanan, Ingersoll & Rooney PC

(57) ABSTRACT

To provide hexaester of bispentaerythritol monoformal, which is a mixed ester of bispentaerythritol monoformal represented by the following formula (I), and carboxylic acids:
(Continued)

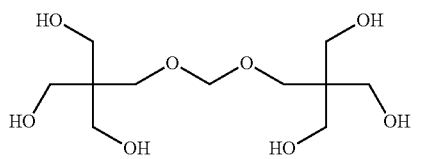

Formula (I)

wherein the carboxylic acids comprise C9 branched aliphatic monocarboxylic acid, and any one of carboxylic acids selected from C4 to C8 aliphatic monocarboxylic acids. The hexaester is used as one component of a refrigerant oil composition, and gives excellent characteristics, such as oxidation stability, lubricity, and low temperature properties, to a refrigerant oil composition.

4 Claims, 4 Drawing Sheets

(51) Int. Cl.
  *C09K 5/04* (2006.01)
  *C10M 105/38* (2006.01)
  *C10M 171/00* (2006.01)
(52) U.S. Cl.
  CPC ... *C10M 171/008* (2013.01); *C09K 2205/122* (2013.01); *C10M 2207/2835* (2013.01); *C10N 2220/022* (2013.01); *C10N 2220/028* (2013.01); *C10N 2230/02* (2013.01); *C10N 2230/06* (2013.01); *C10N 2230/08* (2013.01); *C10N 2230/10* (2013.01); *C10N 2240/30* (2013.01)

(56) References Cited

U.S. PATENT DOCUMENTS 9,365,484 B2 * 6/2016 Nakayama ........... C10M 105/38
2012/0024007 A1    2/2012 Ota et al.

FOREIGN PATENT DOCUMENTS

| JP | 2009-79141 A | 4/2009 |
| JP | 2009-79144 A | 4/2009 |
| JP | 2011-195631 A | 10/2011 |
| JP | 2012-31239 A | 2/2012 |
| JP | 4936656 B2 | 3/2012 |
| JP | 2012-102046 A | 5/2012 |

OTHER PUBLICATIONS

Written Opinion (PCT/ISA/237) mailed on Dec. 24, 2013, by the Japanese Patent Office as the International Searching Authority for International Application No. PCT/JP2013/078513.

International Search Report (PCT/ISA/210) mailed on Jan. 7, 2014, by the Japanese Patent Office as the International Searching Authority for International Application No. PCT/JP2013/078512.

Written Opinion (PCT/ISA/237) mailed on Jan. 7, 2014, by the Japanese Patent Office as the International Searching Authority for International Application No. PCT/JP2013/078512.

"The Tribology," Jul. 1998, pp. 45-47.

R. Hunter et al., "Synthesis of formaldehyde bis(pentaerythritol) acetal (BPMF)", South African Tydskr. Chem., Jul. 1991, pp. 122-124, vol. 44, Issue 4.

* cited by examiner

HEXAESTER OF MONO-FORMAL BIS PENTAERYTHRITOL

TECHNICAL FIELD

The present invention relates a hexaester of bispentaerythritol monoformal, which is excellent in oxidation stability, and a refrigerant oil composition, which contains the hexaester of bispentaerythritol monoformal, and has excellent characteristics, such as oxidation stability, lubricity, and low temperature properties.

BACKGROUND ART

Recently, hydrofluorocarbon(s) (HFC) having the ozone depletion potential of 0, and lower global-warming potential (GWP) has been used as a refrigerant for a refrigerator and the like. HFC is a stable refrigerant compared to chlorofluorocarbon(s) (CFC) and hydrochlorofluorocarbon(s) (HCFC), and does not largely affect to lubricant oil, an organic material, and a metal. On the other hand, HFC does not have sufficient lubricity, and thus refrigerant oil for HFC is required to have sufficient lubricity. Moreover, the heat generated at a sliding portion accelerates thermal and/or oxidative degradation of refrigerant oil. Therefore, refrigerant oil having high thermal and chemical stability is desired (NPL 1).

And a refrigerant oil is typically circulated together with a refrigerant through part of the refrigeration cycle, and thus the refrigerant oil is exposed to a high temperature range and a low temperature range. In the low temperature range, particularly, part of the refrigerant oil discharged from a compressor may be retained. If the refrigerant oil is exposed in the low temperature range for a long period, the refrigerant oil is crystallized to thereby reduce a circulating amount of the refrigerant in the refrigeration cycle, leading to a cooling failure. Accordingly, it is extremely important to develop refrigerant oil, which is highly stable without precipitating over a long period even in the low temperature range, in view of reliability of a refrigeration device (PTL 1).

Hexaester which is made by reacting dipentaerythritol, with 3,5,5-trimethylhexanoic acid and 2-ethylhexanoic acid is disclosed in PTL 2 as an additive polyol ester of refrigerant oil, and in PTL 3 as a lubricant base oil for compressor refrigeration system. However, the aforementioned hexaester does not satisfy oxidation stability.

CITATION LIST

Patent Literature

PTL 1: Japanese Patent (JP-B) No. 4936656
PTL 2: Japanese Patent Application Laid-Open (JP-A) No. 2012-31239
PTL 3: JP-A No. 04-72390

Non-Patent Literature

NPL 1: "The Tribology," 1998, July, p. 45

SUMMARY OF INVENTION

Technical Problem

An object of the present invention is to provide a hexaester of bispentaerythritol monoformal, which has excellent oxidation stability, and a refrigerant oil composition, which contains the hexaester of bispentaerythritol monoformal, has excellent characteristics, such as oxidation stability, lubricity, and low temperature properties.

Solution to Problem

The present invention provides the following [1] to [4].
[1] Hexaester of bispentaerythritol monoformal, which is a mixed ester of bispentaerythritol monoformal represented by the following formula (I), and carboxylic acids:

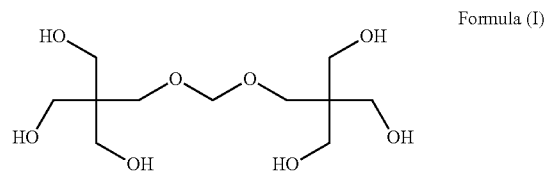

Formula (I)

wherein the carboxylic acids comprise C9 branched aliphatic monocarboxylic acids, and any one of carboxylic acids selected from C4 to C8 aliphatic monocarboxylic acids.
[2] The hexaester of bispentaerythritol monoformal according to [1], wherein the C9 branched aliphatic monocarboxylic acid is 3,5,5-trimethylhexanoic acid.
[3] A refrigerant oil composition, comprising the hexaester of bispentaerythritol monoformal according to any one of [1] or [2].
[4] A working fluid composition for refrigerators, comprising:
the refrigerant oil composition according to [3]; and
a refrigerant.

Advantageous Effects of Invention

The present invention can provide a hexaester of bispentaerythritol monoformal, which is excellent in oxidation stability, and a refrigerant oil composition, which contains the hexaester of bispentaerythritol monoformal, has excellent characteristics, such as oxidation stability, lubricity, and low temperature properties.

DESCRIPTION OF EMBODIMENTS

Figure 1:
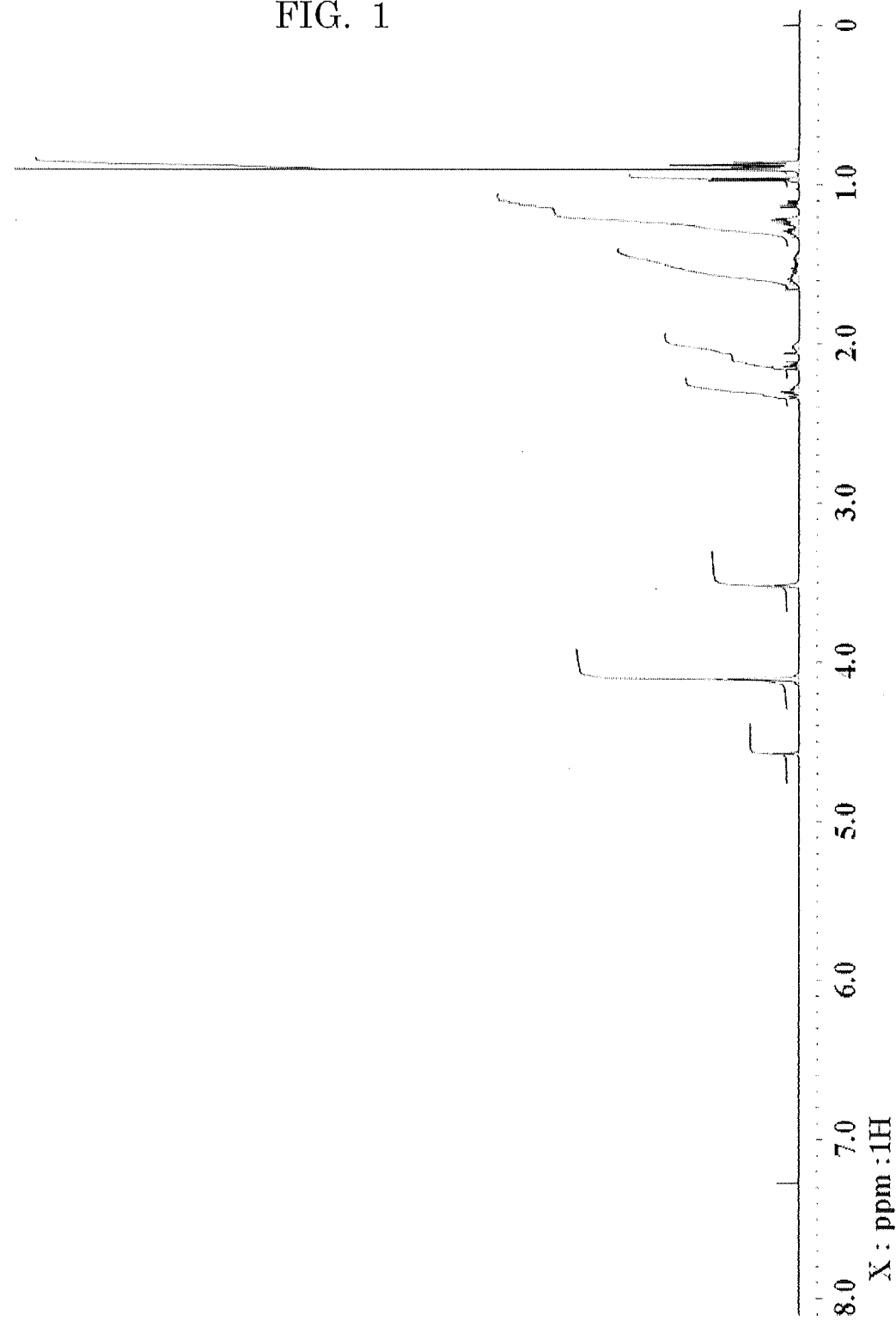
FIG. 1 is a chart depicting the NMR spectrum of the hexaester of bispentaerythritol monoformal, obtained in Example 1.

The hexaester of bispentaerythritol monoformal of the present invention is a mixed ester which is made by reacting bispentaerythritol monoformal represented by the following formula (I), and carboxylic acid:

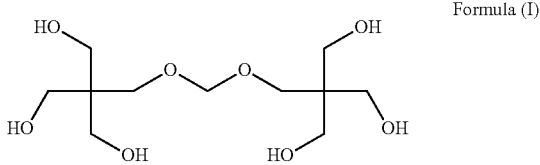 [SMILES: OCC(CO)(CO)COCOCC(CO)(CO)CO]

Formula (I)

where the carboxylic acid is C9 branched aliphatic monocarboxylic acid, and any one of carboxylic acids selected from C4 to C8 aliphatic monocarboxylic acids.

The carboxylic acid constituting the hexaester of bispentaerythritol monoformal of the present invention is referred to as constituent carboxylic acid(s), hereinafter.

The hexaester of the present invention includes each of the following embodiments (i) to (iii):
(i) Hexaester of bispentaerythritol monoformal, in which the constituent carboxylic acid(s) in one molecule contains both C9 branched aliphatic monocarboxylic acid, and one selected from C4 to C8 aliphatic monocarboxylic acids.
(ii) A mixture of hexaester which is made by reacting bispentaerythritol monoformal and C9 branched aliphatic monocarboxylic acid, and hexaester which is made by reacting bispentaerythritol monoformal and one selected from C4 to C8 aliphatic monocarboxylic acids.
(iii) A mixture of (i) and (ii).

The hexaester of bispentaerythritol monoformal of the present invention may contain, as impurities, partial ester of the bispentaerythritol monoformal, in which part of hydroxyl groups are remained as hydroxyl groups without being esterified.

Examples of C9 branched aliphatic monocarboxylic acid constituting the hexaester of bispentaerythritol monoformal of the present invention include one compound selected from 2-methyloctanoic acid, 2,2-dimethylheptanoic acid, 2-propyl-4-methylpentanoic acid, and 3,5,5-trimethylhexanoic acid. Among them, 3,5,5-trimethylhexanoic acid is preferable.

Examples of any one of the carboxylic acids selected from C4 to C8 aliphatic monocarboxylic acids constituting the hexaester of bispentaerythritol monoformal of the present invention comprise butyric acid, pentanoic acid, hexanoic acid, heptanoic acid, octanoic acid, isobutyric acid, 2-methylbutyric acid, 3-methylbutyric acid, 2,2-dimethylpropanoic acid, 2-ethylbutyric acid, 2-methylpentanoic acid, 4-methylpentanoic acid, 2-methylhexanoic acid, 2-ethylpentanoic acid, 2-ethyl-2-methylbutyric acid, 2,2-dimethylpentanoic acid, 2-methylheptanoic acid, 2-ethylhexanoic acid, 3-ethylhexanoic acid, 2-ethyl-2-methylpentanoic acid, and 2-ethyl-4-methylpentanoic acid. Among them, pentanoic acid, isobutyric acid, 3-methylbutyric acid, and 2-ethylhexanoic acid are preferable in view of availability thereof.

A molar ratio of the C9 branched aliphatic monocarboxylic acid to any one of the carboxylic acids selected from C4 to C8 aliphatic monocarboxylic acids (C9 branched aliphatic monocarboxylic acid: any one of the carboxylic acids selected from C4 to C8 aliphatic monocarboxylic acids) is preferably in the range of 90:10 to 10:90, more preferably in the range of 80:20 to 30:70, in view of oxidation stability, lubricity, and low temperature properties.

Next, a production method of the hexaester of bispentaerythritol monoformal of the present invention is explained through examples thereof.

Bispentaerythritol monoformal constituting the hexaester of bispentaerythritol monoformal according to the invention may be produced in accordance with the method (e.g., the method disclosed in the non-latent literature "South African Journal of Chemistry", 1991, vol. 44, no. 4, p. 122): by triacetylating pentaerythritol with acetic anhydride, condensing the obtained pentaerythritol triacetate with dimethoxy methane in the presence of an acid catalyst, and carrying out hydrolysis of acetyl groups of the obtained condensate. Moreover, the bispentaerythritol monoformal can be obtained in accordance with the method (e.g., the method disclosed in U.S. Pat. No. 2,464,430): by allowing acetaldehyde and formaldehyde to react with each other in the presence of a base to produce pentaerythritol, and extracting bispentaerythritol monoformal generated in the process of the reaction as a by-product using butyl acetate. As for another method, the bispentaerythritol monoformal can be obtained by allowing pentaerythritol and 1,1,1-trimethoxyethane to react with each other to obtain a compound (the below-described compound (i)), allowing the obtained compound and dibromomethane to react with each other in the presence of a base to obtain a compound (the below-described compound (ii)), and carrying out hydrolysis of orthoester group(s) of the obtained compound (the compound (ii)), as described in Production Example 1, which is described later.

The hexaester of bispentaerythritol monoformal of the present invention can be produced, for example, by allowing bispentaerythritol monoformal, C9 branched aliphatic monocarboxylic acid, and any one of the carboxylic acids selected from C4 to C8 aliphatic monocarboxylic acids to react with each other for 5 hours to 60 hours at 120° C. to 300° C. (this method is referred to as the production method 1, hereinafter). In this procedure, both carboxylic acids may be added simultaneously, or each of the carboxylic acids may be added successively.

Catalyst(s) may be used in the production method 1. Examples of the catalyst include mineral acids, organic acids, Lewis acids, organic metals, and solid acids. Specific examples of the mineral acid include hydrochloric acid, hydrofluoric acid, sulfuric acid, phosphoric acid, nitric acid, and the like. Specific examples of the organic acid include p-toluenesulfonic acid, benzenesulfonic acid, butanesulfonic acid, propanesulfonic acid, ethanesulfonic acid, methanesulfonic acid, and the like. Specific examples of the Lewis acid include boron trifluoride, aluminium chloride, tin tetrachloride, titanium tetrachloride, and the like. Specific examples of the organic metal include tetrapropoxy titanium, tetrabutoxy titanium, tetrakis(2-ethylhexyloxy)titanium, and the like. Examples of the solid acid include a cation-exchange resin and the like.

In the production method 1, the reaction is preferably carried out with removing water produced during the reaction from a reaction mixture. Moreover, a total amount of C9 branched aliphatic monocarboxylic acid, and any one of the carboxylic acids selected from C4 to C8 aliphatic monocarboxylic acids is preferably 1.1 mol to 1.4 mol relative to 1 mol of hydroxyl groups of bispentaerythritol monoformal.

Moreover, the hexaester of bispentaerythritol monoformal of the present invention can be also produced, for example, by allowing bispentaerythritol monoformal, anhydride of C9 branched aliphatic monocarboxylic acid, and anhydride of any one of the carboxylic acids selected from C4 to C8 aliphatic monocarboxylic acids to react for 1 hour to 10 hours at 50° C. to 100° C. (this method is referred to as the production method 2, hereinafter). In this procedure, both carboxylic acids may be added simultaneously, or each of the carboxylic acids may be added successively.

Catalyst(s) may be used in the production method 2. Examples of the catalyst include organic bases, organic salts, and solid acids. Specific examples of the organic base include pyridine, N,N-dimethyl-4-aminopyridine, and the like. Specific examples of the organic salt include sodium acetate, scandium (III) trifluoromethanesulfonyl imide, trimethylsilyl trifluoromethanesulfonate, and the like. Specific examples of the solid acid include a cation-exchange resin and the like.

In the production method 2, a total amount of anhydride of C9 branched aliphatic monocarboxylic acid, and anhydride of any one of the carboxylic acids selected from C4 to C8 aliphatic monocarboxylic acids is preferably 0.5 mol to 1.4 mol relative to 1 mol of hydroxyl groups of bispentaerythritol monoformal.

In the production methods 1 and 2, the reactivities of C9 branched aliphatic monocarboxylic acid or anhydride thereof, and any one of the carboxylic acids selected from C4 to C8 aliphatic monocarboxylic acids or anhydride thereof to bispentaerythritol monoformal may be different. Therefore, the molar ratio of the C9 branched aliphatic monocarboxylic acid and any one of the carboxylic acids selected from C4 to C8 aliphatic monocarboxylic acids, in the resulting hexaester of bispentaerythritol monoformal may be different from the molar ratio thereof used to prduce the hexaester of bispentaerythritol monoformal.

Solvent(s) may be used in the production methods 1 and 2. Examples of the solvent include hydrocarbon-based solvents, such as benzene, toluene, xylene, hexane, heptane, isohexane, isooctane, isononane, decane, and the like.

In the production methods 1 and 2, the hexaester of bispentaerythritol monoformal of the present invention may be optionally purified after the reaction by a method typically used in synthetic organic chemistry (e.g., washing with water and/or an alkali aqueous solution, a treatment with an activated carbon or an adsorbent, various chromatography, and distillation).

Since the hexaester of bispentaerythritol monoformal of the present invention is composed of bispentaerythritol monoformal, the C9 branched aliphatic monocarboxylic acid, and any one of the carboxylic acids selected from C4 to C8 aliphatic monocarboxylic acids, the hexaester has excellent characteristics, such as oxidation stability. Moreover, the hexaester of bispentaerythritol monoformal of the present invention has sufficient low temperature properties, sufficient low temperature fluidity, and sufficient lubricity.

The refrigerant oil composition of the present invention is a refrigerant oil composition containing the hexaester of bispentaerythritol monoformal of the present invention. And the refrigerant oil composition is composed of only the hexaester, or composed of the hexaester and base oils for a refrigerant oil.

When the hexaester of bispentaerythritol monoformal of the present invention is used as one component of the refrigerant oil composition, the presence of acid in the hexaester may cause corrosion of a metal used for a refrigeration system and a pipe and decrease stability of the hexaester. Therefore, the acid number of the hexaester is preferably 0.5 mgKOH/g or lower, more preferably 0.1 mgKOH/g or lower. When an amount of hydroxyl groups in the hexaester is large, the refrigerant oil is clouded at low temperature, and an undesirable phenomenon, such as a clogging of a capillary device of a refrigeration cycle, is caused. Therefore, a hydroxyl number of the hexaester is preferably 20 mgKOH/g or lower, more preferably 10 mgKOH/g or lower.

When the hexaester of bispentaerythritol monoformal of the present invention is used as one component of the refrigerant oil composition, excellent characteristics, such as oxidation stability, lubricity, and low temperature properties, can be provided to the refrigerant oil composition.

The hexaester of bispentaerythritol monoformal of the present invention is determined by an analysis method, such as nuclear magnetic resonance (which is referred to as NMR hereinafter), gas chromatography (which is referred to as GC hereinafter), and gas chromatography-mass spectrometry (which is referred to as GC-MS hereinafter). In the refrigerant oil composition of the present invention, the hexaester of bispentaerythritol monoformal of the present invention contained in the refrigerant oil composition is determined by the similar analysis methods. Optionally, the hexaester of bispentaerythritol monoformal is separated from the refrigerant oil composition in advance by a method, such as column chromatography, distillation, solvent extraction, crystallization, and the like. In this manner, the determination can be performed easily.

An amount of the hexaester of bispentaerythritol monoformal of the present invention in the refrigerant oil composition of the present invention is not particularly limited, provided that it does not adversely affect various characteristics, such as lubricity, low temperature properties, oxidation stability, and the like. In the case where the refrigerant oil composition contains the hexaester, and base oil for refrigerant oil, an amount of the hexaester in the refrigerant oil composition is preferably 0.1 weight % to 50 weight %, more preferably 1 weight % to 30 weight %, and even more preferably 1 weight % to 10 weight %.

Examples of the base oil for refrigerant oil used in the refrigerant oil composition of the present invention include mineral oil, and synthetic base oil.

Examples of the mineral oil include paraffinic-base crude oil, intermediate-base crude oil, naphthenic-base crude oil, and the like. Moreover, refined oil, obtained by refining any of the above-listed oil via distillation and the like may also be used.

Examples of the synthetic base oil include poly-α-olefins (e.g., polybutene, polypropylene, and α-olefin oligomers having 8 to 14 carbon atoms), aliphatic esters other than the hexaester of bispentaerythritol monoformal of the present invention (e.g., fatty acid monoesters, fatty acid esters of polyhydric alcohols, and aliphatic polybasic acid esters), aromatic esters (e.g., aromatic monoesters, aromatic esters of polyhydric alcohols, and aromatic polybasic acid esters), polyalkylene glycols, polyvinyl ethers, polycarbonates, alkyl benzenes, and the like. Examples of polyhydric alcohol used in the fatty acid esters include hindered alcohols, such as pentaerythritol, polypentaerythritol (e.g., a condensate of pentaerythritol, such as dipentaerythritol, tripentaerythritol, and tetrapentaerythritol), neopentyl glycol, trimethylol propane, and the like. Examples of fatty acid include C4-C18 straight-chain or branched-chain aliphatic monocarboxylic acid.

Specific examples of the fatty acid ester of the polyhydric alcohol include: ester of pentaerythritol, isobutyric acid, and 2-ethylhexanoic acid; and ester of pentaerythritol, isobutyric acid, and 3,5,5-trimethylhexanoic acid; ester of pentaerythritol, pentanoic acid, and 3,5,5-trimethylhexanoic acid; ester of pentaerythritol, pentanoic acid, heptanoic acid, and 3,5, 5-trimethylhexanoic acid; ester of pentaerythritol, 2-methylbutyric acid, and 2-ethylhexanoic acid; ester of pentaerythritol, 3-methylbutyric acid, and 3,5,5-trimethylhexanoic acid; ester of pentaerythritol, 2-ethylhexanoic acid, and 3,5,5-trimethylhexanoic acid; ester of dipentaerythritol, isobutyric acid, and 2-ethylhexanoic acid; ester of dipentaerythritol, isobutyric acid, and 3,5,5-trimethylhexanoic acid; ester of dipentaerythritol, pentanoic acid, and 3,5,5-trimethylhexanoic acid; ester of dipentaerythritol, pentanoic acid, heptanoic acid, and 3,5,5-trimethylhexanoic acid; ester of dipentaerythritol, 2-methylbutyric acid, and 2-ethylhexanoic acid; ester of dipentaerythritol, 3-methylbutyric acid, and 3,5,5-trimethylhexanoic acid; ester of dipentaerythritol, 2-ethylhexanoic acid, and 3,5,5-trimethylhexanoic acid; ester of neopentyl glycol, isobutyric acid, and 2-ethylhexanoic acid; ester of neopentyl glycol, isobutyric acid, and 3,5,5-trimethylhexanoic acid; ester of neopentyl glycol, and 2-ethylhexanoic acid; and a mixture of two or more selected from those listed above.

The refrigerant oil composition of the present invention may optionally further comprise lubricant additive(s). Examples of the lubricant additive include a metal deactivator, an antioxidant, a wear-reducing agent (e.g., an anti-wear agent, an anti-seizure agent, and an extreme-pressure agent), a friction modifier, an acid scavenger, a rust preventative agent, an anti-foaming agent, and the like. The content of each additive in the refrigerant oil composition is preferably 0.001 weight % to 5 weight %.

Examples of a metal deactivator include benzotriazole (referred to as BZT hereinafter), and N,N'-disalicylidene-1, 2-diaminopropane. The metal deactivator is used by being dissolved in a refrigerant oil composition, for the purpose of prolonging the life of the refrigerant oil composition, or the device to which the refrigerant oil composition is used. BZT typically has low solubility to mineral oil and/or synthetic oil (JP-A No. 59-189195), and thus an amount thereof for use may be limited. However, the addition of the hexaester of bispentaerythritol monoformal of the present invention makes it possible to improve the solubility of BZT to the refrigerant oil composition, and thus an amount of BZT for use can be increased.

Since the refrigerant oil composition of the present invention contains the hexaester of bispentaerythritol monoformal, the refrigerant oil composition has excellent characteristics, such as oxidation stability, lubricity, low temperature properties, and the like.

The refrigerant oil composition is used for a refrigeration system of a domestic air conditioner. However, there is a case where air is included in a refrigeration cycle when the refrigeration system is installed, and thus the refrigerant oil composition is influenced by oxygen. Therefore, the refrigerant oil composition requires high oxidation stability.

The oxidation stability of the hexaester of bispentaerythritol monoformal of the present invention, and the refrigerant oil composition of the present invention can be evaluated by measuring RBOT life by an oxidation stability test. In the present specification, the RBOT life is measured by the method described in the test example, which is described later.

In view of the protection of the environment, moreover, CFC refrigerants or HCFC refrigerants has been replaced with HFC refrigerants. However, the HFC refrigerants have a problem in lubricity, as the HFC refrigerants do not contain chlorine in the molecular structure thereof. Therefore, more excellent lubricity is required for a refrigerant oil composition used for the HFC refrigerants. The lubricity includes friction-reducing properties, wear-reducing properties (anti-wear properties), extreme-pressure properties, and the like.

In the case where the refrigerant oil composition is stored for a long period or used at a place having a significant temperature change, the refrigerant oil composition is preferably not volatile at the high temperature range, and is not preferably solidified or precipitated at the low temperature range. The temperature range is not particularly limited, but preferred is a refrigerant oil composition that can be stably used at around 150° C. for the high temperature range, and at around −20° C. for the low temperature range. In the present specification, the properties of the oil composition where the oil composition is not solidified or precipitated at the low temperature range are determined as low temperature properties.

Moreover, the refrigerant oil composition of the present invention has sufficient thermal stability, and sufficient oxidation/hydrolysis stability.

The working fluid composition for refrigerators is a working fluid composition containing the refrigerant oil composition of the present invention, and a refrigerant. A blending ratio between the refrigerant oil composition and the refrigerant is not particularly limited, but an amount of the refrigerant oil composition is preferably 1 part by weight to 1,000 parts by weight, more preferably 2 parts by weight to 800 parts by weight, relative to 100 parts by weight of the refrigerant.

Examples of the refrigerant of the working fluid composition for refrigerators include a fluorine-containing refrigerant, a natural refrigerant, and the like.

Examples of the fluorine-containing refrigerant include: hydrofluorocarbon, such as difluoromethane (HFC32), trifluoromethane (HFC23), pentafluoroethane (HFC125), 1,1,2,2-tetrafluoroethane (HFC134), 1,1,1,2-tetrafluoroethane (HFC134a), 1,1,1-trifluoroethane (HFC143a); unsaturated fluorohydrocarbon, such as 2,3,3,3-tetrafluoropropene (HFO1234yf), 1,3,3,3-tetrafluoropropene (HFO1234ze), 1,2,3,3-tetrafluoropropene (HFO1234ye), and 1,2,3,3,3-pentafluoropropene (HFO1225ye); and a mixture thereof.

Examples of the natural refrigerant include hydrocarbon (e.g., propane, butane, and isobutane), carbon dioxide, ammonia, and the like.

The hexaester of bispentaerythritol monoformal of the present invention may be used in engine oil, gear oil, motor oil used for hybrid cars or electric cars, grease, additives for lubricant oil, a detergent of metal parts, a plasticizer, or a cosmetic product, in addition to the refrigerant oil and the working fluid composition for refrigerators. Moreover, the refrigerant oil composition and the working fluid composition for refrigerators of the present invention are suitably used for domestic air conditioners, packaged air conditioners, automotive air conditioners, dehumidifiers, refrigerators, freezers, fridge-freezers, vending machines, display cases, or refrigeration systems of chemical plants.

EXAMPLES

The present invention is more specifically explained through production examples, examples, comparative examples, and test examples, hereinafter. However, the invention is not limited to the following examples.

<NMR>

The bispentaerythritol monoformal obtained in Production Example 1, and the esters and the refrigerant oil compositions obtained in Production Example 4, and Examples 1 to 5, 10, and 11, and Comparative Example 1 were subjected to measurement of NMR. The NMR measurement was performed by means of the following measuring device, and in the following measurement method.

Measuring device; GSX-400 (400 MHz) (manufactured by JOEL Ltd.)

Measurement method;

Nucleus type: $^1$H

Reference standard: tetramethylsilane

Solvent: $CDCl_3$ or $d_6$-DMSO

<GC>

The purity of the bispentaerythritol monoformal obtained in Production Example 1, and the main peak retention time of the esters and the refrigerant oil compositions obtained in Examples 1 to 5, 10, and 11 were measured by GC. The GC measurement was performed by means of the following measuring device under the following measuring conditions, after preparing a test liquid in the following method. Preparation method of test liquid;

1) Preparation of Test Liquid of Bispentaerythritol Monoformal

A reactor was charged with 10 mg of the bispentaerythritol monoformal obtained in Production Example 1 below, and 1 mL of a trimethylsilylating agent (product name: TMS-HT, manufactured by Tokyo Chemical Industry Co., Ltd.), and the resulting mixture was stirred for 10 minutes at 80° C. After the reaction was completed, the reaction liquid was filtered with a membrane filter (PTFE, 0.5 μm). The resulting filtrate was provided as a test liquid.

2) Preparation of Test Liquid of Ester and Refrigerant Oil Composition

A test liquid was prepared by blending 0.1 g of each of the esters or the refrigerant oil compositions obtained in Examples 1 to 11, and Comparative Examples 2 to 3 below, with 0.5 g of acetone.

Measuring device: Agilent 7890A (manufactured by Agilent Technologies, Inc.)

Measuring conditions:

Column: HP-5 (length: 30 m, I.D.: 0.320 mm, film thickness: 0.25 μm) (manufactured by Agilent Technologies, Inc.)

Carrier gas: nitrogen, flow rate 1.0 mL/min

INJ/DET temperature: 330° C./350° C.

Injection mode: split mode (1 μL injection, split ratio: 1/50)

Detector: FID

Temperature program: start with an initial temperature of 100° C., a ramp rate of 10° C./min, a final temperature of 325° C., and a final hold time of 97.5 min.

<GC-MS>

The esters obtained in Examples 1, 3 and 4 below was measured by GC-MS. The GC-MS measurement was performed by means of the following measuring device under the following measuring conditions.

Measuring devices: Agilent 7890A (manufactured by Agilent Technologies, Inc.)

JOEL JMS-T100GC$_v$ mass spectrometer (manufactured by JOEL Ltd.)

Measuring conditions:

Column: DB-5 (length: 30 m, I.D.: 0.25 mm, film thickness: 0.25 μm) (manufactured by Agilent Technologies, Inc.)

Carrier gas: helium, flow rate 1.0 mL/min

Injection temperature: 300° C.

Injection mode: split mode (split ratio: 1/50)

Ionization method: CI (reagent gas; ammonia), EI

Temperature program: start with an initial temperature of 100° C., a ramp rate of 10° C./min, a final temperature of 325° C., and a final hold time of 97.5 min.

<High Performance Liquid Chromatography>

The purity of the bispentaerythritol monoformal obtained in Production Example 1 below was measured by high performance liquid chromatography (referred to as LC, hereinafter). The LC measurement was performed by means of the following measuring device under the following measuring conditions, after preparing a test liquid by the following method.

Preparation method of test liquid; A test liquid was prepared by blending 2.5 mg of the bispentaerythritol monoformal obtained in Production Example 1 below, and 497.5 mg of 0.1 weight % phosphoric acid aqueous solution.

Measuring device: Agilent 1200 Series (manufactured by Agilent Technologies, Inc.)

Measuring conditions:

Column: YMC-Pack ODS-AM (spherical particle, particle size: 5 μm, pore size: 12 nm, length: 300 mm, I.D.: 4.6 mm) (manufactured by YMC CO., LTD.)

Solvent: 0.1 weight % phosphoric acid aqueous solution, flow rate 0.7 mL/min

Column temperature: 40° C.

Injection volume of sample: 5 μL

Detector: RI

Production Example 1

Production of Bispentaerythritol Monoformal (1) Production of Compound (i)

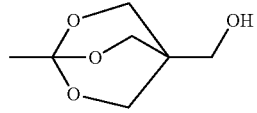

Compound (i)

A reactor equipped with a Dean-Stark trap was charged with 544.6 g of pentaerythritol (4.00 mol, product name: Pentarit-S, manufactured by Koei Chemical Company, Limited), 480.6 g of 1,1,1-trimethoxyethane (4.00 mol, manufactured by Tokyo Chemical Industry Co., Ltd.), 6.9 g of p-toluenesulfonic acid monohydrate (0.04 mol, manufactured by Tokyo Chemical Industry Co., Ltd.), and 2 L of toluene, and the mixture was stirred for 14 hours at 70° C. to 100° C. The Dean-Stark trap was replaced with a dropping funnel filled with molecular sieves, followed by stirring the mixture for 10 hours at 110° C. to 120° C. After completing the reaction, the reaction product was condensed, and 20.4 g of triethylamine was added to the resulting condensed product. The resultant was then crystallized with 2.6 L of dichloromethane, to thereby yield 234.6 g of a compound (i).

$^1$H-NMR (CDCl$_3$, δ ppm); 1.46 (s, 3H), 3.47 (s, 2H), 4.02 (s, 6H)

(2) Production of Compound (ii)

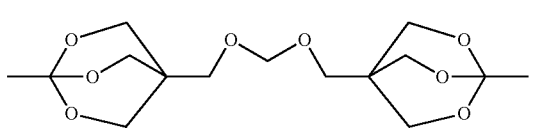

Compound (ii)

A reactor was charged with 72.8 g of sodium hydride dispersed in liquid paraffin (concentration of sodium hydride: 60 weight %, manufactured by Tokyo Chemical Industry Co., Ltd.), 224.2 g of the compound (i), and 3.5 L of dimethylformamide. To this, 121.7 g of dibromomethane (0.70 mol, manufactured by Tokyo Chemical Industry Co., Ltd.) was dropped at 0° C. The resulting mixture was stirred for 1 hour at room temperature, followed by adding 130 mL of methanol. After completing the reaction, the reaction product was condensed at 70° C. under the reduced pressure of 1.3 kPa. The condensed product was diluted with 2.5 L of dichloromethane, and then washed with 1 L of water. The organic layer was condensed, and the condensed product was crystallized with 10.6 L of methanol, to thereby yield 62.7 g of a compound (ii).

$^1$H-NMR (CDCl$_3$, δ ppm); 1.46 (s, 6H), 3.24 (s, 4H), 3.98 (s, 12H), 4.53 (s, 2H)

(3) Production of Bispentaerythritol Monoformal

A reactor was charged with 78.3 g of the compound (ii), and 320 g of water, and the resulting mixture was stirred for 2 hours at 100° C. Subsequently, 1905.0 g of a strong-base anion exchange resin (product name: DIAION SA11A, manufactured by Mitsubishi Chemical Corporation) was added to the mixture, and the resultant was stirred for 1 hour at room temperature. The reaction product was filtered, followed by condensing the filtrate. The condensed product was crystallized with 1.7 L of ethanol, to thereby yield 53.6 g of bispentaerythritol monoformal. $^1$H-NMR (d$_6$-DMSO, δ ppm); 3.32-3.40 (m, 16H), 4.25 (t, 6H), 4.54 (s, 2H)
The purity measured by GC: 95 area % or greater
The purity measured by LC: 95 area % or greater Production Example 2

Production of 3,5,5-Trimethylhexanoic Anhydride

A reactor was charged with 633.0 g of 3,5,5-trimethylhexanoic acid (4.00 mol, manufactured by KH Neochem Co., Ltd.) and 817.5 g of acetic anhydride (8.00 mol, manufactured by Wako Pure Chemical Industries, Ltd.), and the resulting mixture was stirred for 1 hour at 120° C. After completing the reaction, the reaction product was distilled at 157° C. to 162° C. under the reduced pressure of 0.4 kPa, to thereby yield 496.4 g of 3,5,5-trimethylhexanoic anhydride.

Production Example 3

Production of 2-Ethylhexanoic Anhydride

A reactor was charged with 721.1 g of 2-ethylhexanoic acid (5.00 mol, manufactured by KH Neochem Co., Ltd.) and 919.7 g of acetic anhydride (9.00 mol, manufactured by Wako Pure Chemical Industries, Ltd.), and the resulting mixture was stirred for 1 hour at 120° C. After completing the reaction, the reaction product was distilled at 126° C. to 133° C. under the reduced pressure of 0.1 kPa, to thereby yield 509.8 g of 2-ethylhexanoic anhydride.

Example 1

Production of Hexaester of Bispentaerythritol Monoformal with 3,5,5-Trimethylhexanoic Acid and 2-Ethylhexanoic Acid in Molar Ratio (3,5,5-Trimethylhexanoic Acid/2-Ethylhexanoic Acid) of 50/50 (Hexaester 1)

A reactor was charged with 8.5 g (0.03 mol) of the bispentaerythritol monoformal produced in Production Example 1, 32.2 g (0.11 mol) of the 3,5,5-trimethylhexanoic anhydride produced in Production Example 2, 24.3 g (0.09 mol) of the 2-ethylhexanoic anhydride produced in Production Example 3, and 42.7 g of pyridine (0.54 mol, manufactured by Wako Pure Chemical Industries, Ltd.), and the resulting mixture was degassed by nitrogen bubbling for 15 minutes at room temperature under the reduced pressure of 20 kPa. Subsequently, the mixture, which had been subjected to degassing, was stirred for 6 hours at 90° C. with nitrogen bubbling. After completing the reaction, the reaction product was condensed for 2 hours at 150° C. to 220° C. under the reduced pressure of 1.3 kPa. The condensed product was washed once with 20 mL of an alkaline aqueous solution containing 2 fold moles of sodium hydroxide relative to the acid number of the condensed product, followed by washing three times with 20 mL of water. Then, the resultant was dehydrated for 1 hour at 100° C. under the reduced pressure of 1.3 kPa with nitrogen bubbling. Subsequently, 0.2 g of an adsorbent (product name: KYOWAAD 500, manufactured by Kyowa Chemical Industry Co., Ltd.), and 0.3 g of activated carbon (product name: SHIRASAGI P, manufactured by Japan EnviroChemicals, Ltd.) were added, and the resultant was stirred for 1 hour at 110° C. under the reduced pressure of 1.3 kPa with nitrogen bubbling. Subsequently, the resultant was filtered with a membrane filter (PTFE, 0.2 μm), to thereby yield 24.7 g of Hexaester 1. The NMR spectrum of Hexaester 1 was measured to calculate a molar ratio of 3,5,5-trimethylhexanoic acid and 2-ethylhexanoic acid constituting Hexaester 1. The obtained NMR spectrum chart is presented in FIG. 1. Moreover, Hexaester 1 was subjected to the measurements of GC and GC-MS. From the GC measurement, the retention time (66.3 minutes, 73.1 minutes, 80.7 minutes, 88.7 minutes, 96.6 minutes, 105.5 minutes, 115.5 minutes) of the main peaks was confirmed. From the GC-MS measurement, the main peak retention time, and the fragment thereof were confirmed. The results of GC-MS are presented in Table 1.

TABLE 1

| | Peak | 1-1 | 1-2 | 1-3 | 1-4 | 1-5 | 1-6 | 1-7 |
|---|---|---|---|---|---|---|---|---|
| GC-MS | Retention time (min) | 54.8 | 59.6 | 65.2 | 71.6 | 78.8 | 86.9 | 96.2 |
| | CI m/z [M + NH$_4$]$^+$ | 1,059 | 1,073 | 1,087 | 1,101 | 1,115 | 1,129 | 1,143 |
| | EI m/z | 127, 497 | 127, 141, 497, 511 | 127, 141, 497, 511, 525 | 127, 141, 497, 511, 525, 539 | 127, 141, 511, 525, 539 | 127, 141, 525, 539 | 141, 539 |

Figure 2:
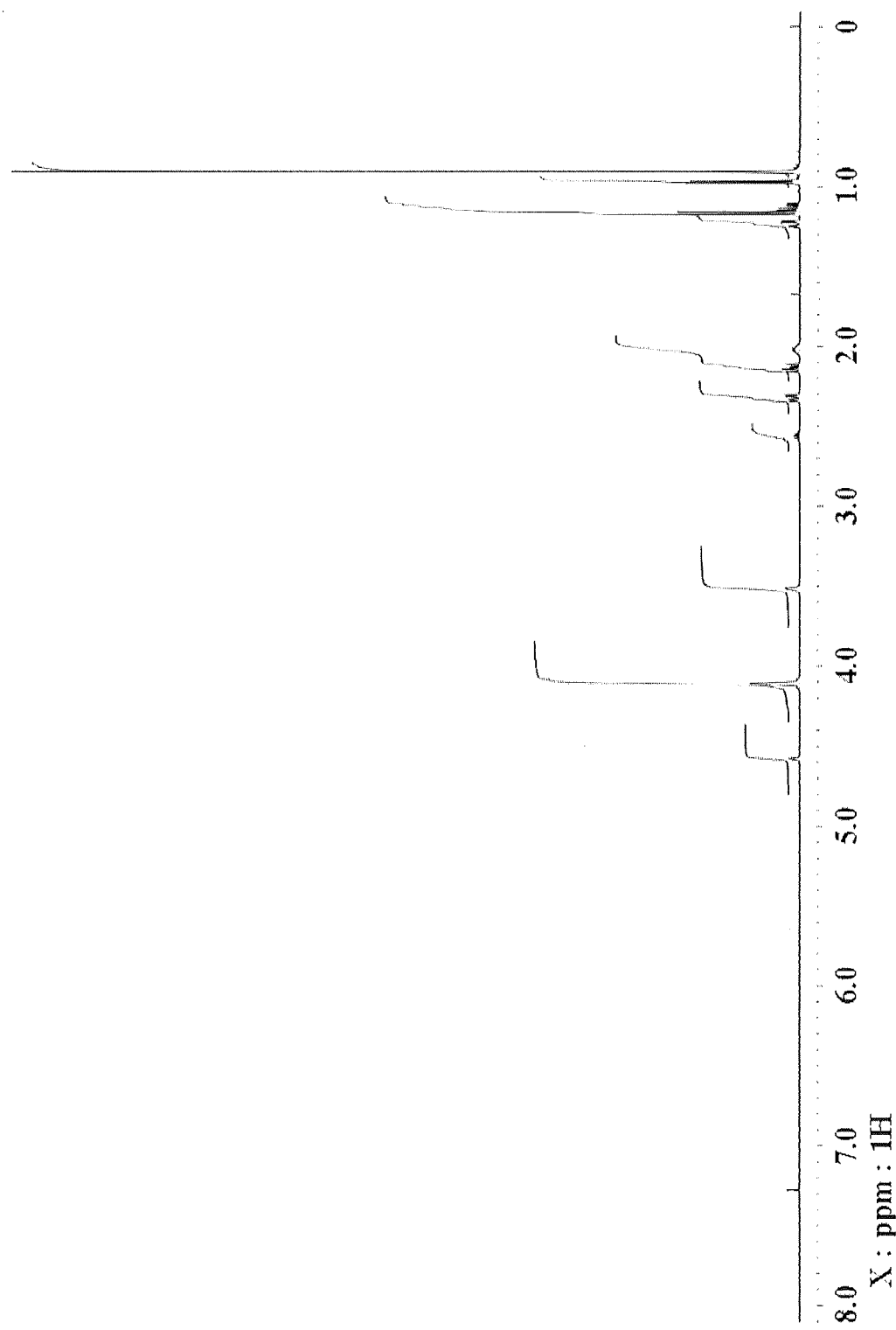
FIG. 2 is a chart depicting the NMR spectrum of the hexaester of bispentaerythritol monoformal, obtained in Example 3.

From Table 1, a compound belong to each peak was assumed as follow:

Peak 1-1 was a peak of hexaester [molecular weight: 1,041 g/mol], in which a number of molecules of the carboxylic acid bonded to one molecule of bispentaerythritol monoformal [3,5,5-trimethylhexanoic acid/2-ethylhexanoic acid] was [0/6]. Peak 1-2 was a peak of hexaester [molecular weight: 1,056 g/mol], in which a number of molecules of the carboxylic acid was [1/5]. Peak 1-3 was a peak of hexaester [molecular weight: 1,070 g/mol], in which a number of molecules of the carboxylic acid was [2/4]. Peak 1-4 was a peak of hexaester [molecular weight: 1,084 g/mol], in which a number of molecules of the carboxylic acid was [3/3]. Peak 1-5 was a peak of hexaester [molecular weight: 1,098 g/mol], in which a number of molecules of the carboxylic presented in FIG. 2. Moreover, Hexaester 3 was subjected to the measurements of GC and GC-MS. From the GC measurement, the retention time (24.6 minutes, 27.9 minutes, 33.2 minutes, 41.9 minutes, 56.2 minutes, 79.5 minutes, 115.7 minutes) of the main peaks was confirmed. From the GC-MS measurement, the main peak retention time, and the fragment thereof were confirmed. The results of GC-MS are presented in Table 2.

TABLE 2

| | Peak | 3-1 | 3-2 | 3-3 | 3-4 | 3-5 | 3-6 | 3-7 |
|---|---|---|---|---|---|---|---|---|
| GC-MS | Retention time (min) | 22.9 | 25.1 | 29.7 | 37.7 | 50.3 | 69.1 | 96.0 |
| | CI m/z $[M + NH_4]^+$ | 722 | 793 | 863 | 933 | 1,003 | 1,073 | 1,143 |
| | EI m/z | 71, 329 | 71, 141, 329, 399 | 71, 141, 329, 399, 469 | 71, 141, 329, 399, 469, 539 | 71, 141, 329, 399, 469, 539 | 71, 141, 399, 469, 539 | 141, 539 | acid was [4/2]. Peak 1-6 was a peak of hexaester [molecular weight: 1,112 g/mol], in which a number of molecules of the carboxylic acid was [5/1]. Peak 1-7 was a peak of hexaester [molecular weight: 1,126 g/mol], in which a number of molecules of the carboxylic acid was [6/0].

Example 2

Production of Hexaester of Bispentaerythritol Monoformal with 3,5,5-Trimethylhexanoic Acid and 2-Ethylhexanoic Acid in Molar Ratio (3,5,5-Trimethylhexanoic Acid/2-Ethylhexanoic Acid) of 74/26 (Hexaester 2)

Hexaester 2 was obtained in the same manner as in Example 1, except that the molar ratio of the bispentaerythritol monoformal, the 3,5,5-trimethylhexanoic anhydride, and the 2-ethylhexanoic anhydride (bispentaerythritol monoformal/3,5,5-trimethylhexanoic anhydride/2-ethylhexanoic anhydride) was changed to 1.00/5.04/1.80. The NMR spectrum of Hexaester 2 was measured to calculate a molar ratio of 3,5,5-trimethylhexanoic acid and 2-ethylhexanoic acid constituting Hexaester 2. Moreover, Hexaester 2 was subjected to the measurement of GC. As a result, peaks were detected at the same retention time to that of Hexaester 1 of Example 1.

Example 3

Production of Hexaester of Bispentaerythritol Monoformal with 3,5,5-Trimethylhexanoic Acid and Isobutyric Acid in Molar Ratio (3,5,5-Trimethylhexanoic Acid/Isobutyric Acid) of 70/30 (Hexaester 3)

Hexaester 3 was obtained in the same manner as in Example 1, except that the 2-ethylhexanoic anhydride was replaced with isobutyric anhydride (manufactured by Wako Pure Chemical Industries, Ltd.), and a molar ratio of the bispentaerythritol monoformal, the 3,5,5-trimethylhexanoic anhydride, and the isobutyric anhydride (bispentaerythritol monoformal/3,5,5-trimethylhexanoic anhydride/isobutyric anhydride) was changed to 1.00/3.75/2.70. The NMR spectrum of Hexaester 3 was measured to calculate a molar ratio of 3,5,5-trimethylhexanoic acid and isobutyric acid constituting Hexaester 3. The obtained NMR spectrum chart is From Table 2, a compound belong to each peak was assumed as follow:

Peak 3-1 was a peak of hexaester [molecular weight: 705 g/mol], in which a number of molecules of the carboxylic acid bonded to one molecule of bispentaerythritol monoformal [3,5,5-trimethylhexanoic acid/isobutyric acid] was [0/6]. Peak 3-2 was a peak of hexaester [molecular weight: 775 g/mol], in which a number of molecules of the carboxylic acid was [1/5]. Peak 3-3 was a peak of hexaester [molecular weight: 845 g/mol], in which a number of molecules of the carboxylic acid was [2/4]. Peak 3-4 was a peak of hexaester [molecular weight: 915 g/mol], in which a number of molecules of the carboxylic acid was [3/3]. Peak 3-5 was a peak of hexaester [molecular weight: 985 g/mol], in which a number of molecules of the carboxylic acid was [4/2]. Peak 3-6 was a peak of hexaester [molecular weight: 1,056 g/mol], in which a number of molecules of the carboxylic acid was [5/1]. Peak 3-7 was a peak of hexaester [molecular weight: 1,126 g/mol], in which a number of molecules of the carboxylic acid was [6/0].

Example 4

Production of Hexaester of Bispentaerythritol Monoformal with 3,5,5-Trimethylhexanoic Acid and Pentanoic Acid in Molar Ratio (3,5,5-Trimethylhexanoic Acid/Pentanoic Acid) of 71/29 (Hexaester 4)

Figure 3:
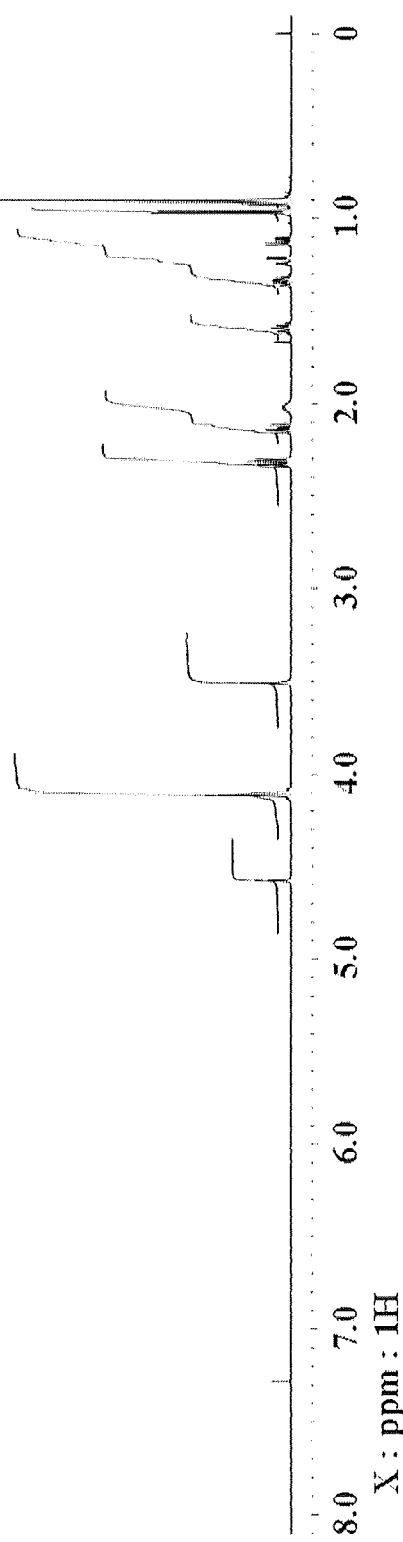
FIG. 3 is a chart depicting the NMR spectrum of the hexaester of bispentaerythritol monoformal, obtained in Example 4.

Hexaester 4 was obtained in the same manner as in Example 1, except that the 2-ethylhexanoic anhydride was replaced with pentanoic anhydride (manufactured by Tokyo Chemical Industry Co., Ltd.), and a molar ratio of the bispentaerythritol monoformal, the 3,5,5-trimethylhexanoic anhydride, and the pentanoic anhydride (bispentaerythritol monoformal/3,5,5-trimethylhexanoic anhydride/pentanoic anhydride) was changed to 1.00/5.76/1.20. The NMR spectrum of Hexaester 4 was measured to calculate a molar ratio of 3,5,5-trimethylhexanoic acid and pentanoic acid constituting Hexaester 4. The obtained NMR spectrum chart is presented in FIG. 3. Moreover, Hexaester 4 was subjected to the measurements of GC and GC-MS. From the GC measurement, the retention time (34.0 minutes, 39.4 minutes, 46.8 minutes, 57.0 minutes, 70.6 minutes, 88.6 minutes, 111.4 minutes) of the main peaks was confirmed. From the GC-MS measurement, the main peak retention time, and the fragment thereof were confirmed. The results of GC-MS are presented in Table 3.

TABLE 3

| Peak | | 4-1 | 4-2 | 4-3 | 4-4 | 4-5 | 4-6 | 4-7 |
|---|---|---|---|---|---|---|---|---|
| GC-MS | Retention time (min) | 30.9 | 35.3 | 41.4 | 49.8 | 61.1 | 76.2 | 96.1 |
| | CI m/z [M + NH$_4$]$^+$ | 807 | 863 | 919 | 975 | 1,031 | 1,087 | 1,143 |
| | EI m/z | 85, 371 | 85, 141, 371, 427 | 85, 141, 371, 427, 483 | 85, 141, 371, 427, 483, 539 | 85, 141, 427, 483, 539 | 85, 141, 483, 539 | 141, 539 |

From Table 3, a compound belong to each peak was assumed as follow:

Peak 4-1 was a peak of hexaester [molecular weight: 789 g/mol], in which a number of molecules of the carboxylic acid bonded to one molecule of bispentaerythritol monoformal [3,5,5-trimethylhexanoic acid/pentanoic acid] was [0/6]. Peak 4-2 was a peak of hexaester [molecular weight: 845 g/mol], in which a number of molecules of the carboxylic acid was [1/5]. Peak 4-3 was a peak of hexaester [molecular weight: 901 g/mol], in which a number of molecules of the carboxylic acid was [2/4]. Peak 4-4 was a peak of hexaester [molecular weight: 957 g/mol], in which a number of molecules of the carboxylic acid was [3/3]. Peak 4-5 was a peak of hexaester [molecular weight: 1,013 g/mol], in which a number of molecules of the carboxylic acid was [4/2]. Peak 4-6 was a peak of hexaester [molecular weight: 1,070 g/mol], in which a number of molecules of the carboxylic acid was [5/1]. Peak 4-7 was a peak of hexaester [molecular weight: 1,126 g/mol], in which a number of molecules of the carboxylic acid was [6/0].

Example 5

Production of Hexaester of Bispentaerythritol Monoformal with 3,5,5-Trimethylhexanoic Acid and 3-Methylbutyric Acid in Molar Ratio (3,5,5-Trimethylhexanoic Acid/3-Methylbutyric Acid) of 66/34 (Hexaester 5)

Figure 4:
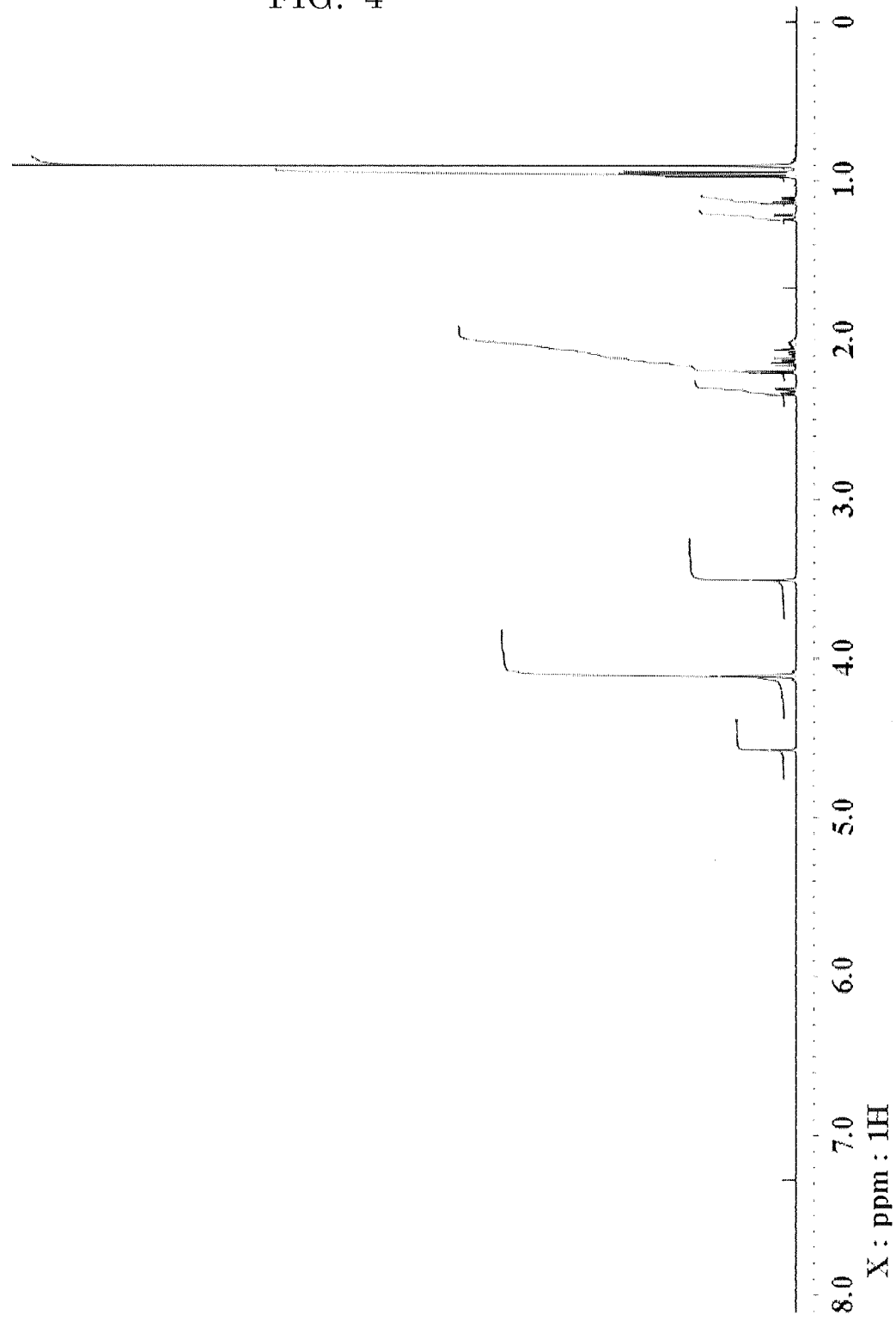
FIG. 4 is a chart depicting the NMR spectrum of the hexaester of bispentaerythritol monoformal, obtained in Example 5.

Hexaester 5 was obtained in the same manner as in Example 1, except that the 2-ethylhexanoic anhydride was replaced with 3-methylbutyric anhydride (manufactured by Tokyo Chemical Industry Co., Ltd.), and a molar ratio of the bispentaerythritol monoformal, the 3,5,5-trimethylhexanoic anhydride, and the 3-methylbutyric anhydride (bispentaerythritol monoformal/3,5,5-trimethylhexanoic anhydride/3-methylbutyric anhydride) was changed to 1.00/3.60/3.00. The NMR spectrum of Hexaester 5 was measured to calculate a molar ratio of 3,5,5-trimethylhexanoic acid and 3-methylbutyric acid constituting Hexaester 5. The obtained NMR spectrum chart is presented in FIG. 4. Moreover, Hexaester 5 was subjected to the measurement of GC. As a result, each peak (retention time: 28.8 minutes, 33.0 minutes, 39.4 minutes, 48.9 minutes, 62.8 minutes, 82.6 minutes, 110.2 minutes) was detected.

Comparative Example 1

Production of Hexaester of Dipentaerythritol with 3,5,5-Trimethylhexanoic Acid and 2-Ethylhexanoic Acid in Molar Ratio (3,5,5-Trimethylhexanoic Acid/2-Ethylhexanoic Acid) is 47/53 (Hexaester A)

A reactor equipped with a Dean-Stark trap was charged with 63.6 g of dipentaerythritol (0.25 mol, product name: Dipentarit, manufactured by Koei Chemical Company, Limited), 122.5 g of 3,5,5-trimethylhexanoic acid (0.77 mol, manufactured by KH Neochem Co., Ltd.), and 148.0 g of 2-ethylhexanoic acid (1.03 mol, manufactured by KH Neochem Co., Ltd.), and the resulting mixture was degassed by nitrogen bubbling for 30 minutes at room temperature under the reduced pressure of 20 kPa. Subsequently, the mixture, which had been subjected to degassing, was stirred for 18 hours at 190° C. to 240° C. with nitrogen bubbling. After completing the reaction, the reaction product was condensed for 1 hour at 210° C. under the reduced pressure of 1.3 kPa. The condensed product was washed once with 100 mL of an alkaline aqueous solution containing 2 fold moles of sodium hydroxide relative to the acid number of the condensed product, followed by washing three times with 100 mL of water. The resulting organic layer was dehydrated for 1 hour at 100° C. under the reduced pressure of 1.3 kPa, with nitrogen bubbling. Subsequently, 0.3 g of an adsorbent (product name: KYOWAAD 500, manufactured by Kyowa Chemical Industry Co., Ltd.), and 2.6 g of activated carbon (product name: SHIRASAGI P, manufactured by Japan EnviroChemicals, Ltd.) were added, and the resultant was stirred for 1 hour at 100° C. under the reduced pressure of 1.3 kPa. Subsequently, the resultant was filtered with a filter aid (product name: Radiolite #500, manufactured by Showa Chemical Industry Co., Ltd.), to thereby yield 210.7 g of Hexaester A. The NMR spectrum of Hexaester A was measured to calculate a molar ratio of 3,5,5-trimethylhexanoic acid and 2-ethylhexanoic acid constituting Hexaester A.

Test Example 1

Measurement of Kinematic Viscosity of Hexaester

The kinematic viscosity of Hexaester 1 to Hexaester 5, and Hexaester A at 40° C. and 100° C. was measured by means of Cannon-Fenske Viscometer in accordance with the method of JIS K2283:2000. The results are presented in Table 4.

Test Example 2

Evaluation of Oxidation Stability of Hexaester (Measurement of RBOT Life)

An oxidation stability test was performed by means of a rotating bomb oxidation tester RBOT-02 (manufactured by Rigo Co., Ltd.). 10 g of the hexaester (Hexaester 1 to Hexaester 5, and Hexaester A), and electrolytic copper wire (diameter: 1.6 mm, length: 3 m) polished with sand paper #400 were placed in a pressure vessel. Subsequently, oxygen was introduced into the pressure vessel until the pressure reached 620 kPa. The pressure vessel was placed in a thermostat bath set to 150° C., and a test was initiated by rotating the pressure vessel at 100 rpm, which was recorded as the starting point of the test. The point where the pressure was declined by 35 kPa from the maximum pressure reached by the pressure vessel was determined as a terminal point. The time from the starting point of the test to the terminal point (RBOT life) was determined. The results are presented in Table 4. The longer RBOT life means that the hexaester has more excellent oxidation stability. In the case where the hexaester is used as one component of a refrigerant oil composition, the refrigerant oil, which has longer RBOT life, can be maintained oxidation stability of the refrigerant oil composition for a longer period.

Test Example 3

Evaluation of Low Temperature Properties of Hexaester (Confirmation of Presence of Solidification and Precipitation at −20° C.)

1 g of hexaester (Hexaester 1 to Hexaester 5) was placed in a glass container, and was left to stand for 24 hours in a thermostat container set to −20° C. After leaving to stand for 24 hours, the presence of solidification and precipitation was confirmed visually. The results are presented below.

Production Example 4

Production of Tetraester of Pentaerythritol with 3,5,5-Trimethylhexanoic Acid and 2-Ethylhexanoic Acid in Molar Ratio (3,5,5-Trimethylhexanoic Acid/2-Ethylhexanoic Acid) of 57/43 (Refrigerant Base Oil A)

Refrigerant Base Oil A was obtained in the same manner as in Comparative Example 1, except that the dipentaerythritol was replaced with pentaerythritol (product name: Pentarit-S, manufactured by Koei Chemical Company, Limited), and a molar ratio of the pentaerythritol, the 3,5,5-trimethylhexanoic acid, and the 2-ethylhexanoic acid (pentaerythritol/3,5,5-trimethylhexanoic acid/2-ethylhexanoic acid) was set to 1.00/2.40/2.40. The NMR spectrum of Refrigerant Base Oil A was measured to calculate a molar ratio of 3,5,5-trimethylhexanoic acid and 2-ethylhexanoic acid constituting Refrigerant Base Oil A.

Example 6

Preparation of Refrigerant Oil Composition 1

Refrigerant Oil Composition 1 was prepared by blending refrigerant Base Oil A produced in Production Example 4

TABLE 4

|  |  | Hexaester 1 (Ex. 1) | Hexaester 2 (Ex. 2) | Hexaester 3 (Ex. 3) | Hexaester 4 (Ex. 4) | Hexaester 5 (Ex. 5) | Hexaester A (Comp. Ex. 1) |
| --- | --- | --- | --- | --- | --- | --- | --- |
|  | Alcohol | BPE | BPE | BPE | BPE | BPE | DPE |
| Ratio of carboxylic acid (molar ratio) | 3,5,5-trimethyl hexanoic acid | 50 | 74 | 70 | 71 | 66 | 47 |
|  | 2-ethyl hexanoic acid | 50 | 26 | — | — | — | 53 |
|  | isobutyric acid | — | — | 30 | — | — | — |
|  | pentanoic acid | — | — | — | 29 | — | — |
|  | 3-methyl butyric acid | — | — | — | — | 34 | — |
| Kinematic viscosity (mm²/sec) | 40° C. | 247 | 368 | 365 | 251 | 397 | 215 |
|  | 100° C. | 19 | 24 | 23 | 20 | 24 | 18 |
|  | RBOT life (min) | 100 | 144 | 142 | 251 | 312 | 58 |

*BPE: bispentaerythritol monoformal
*DPE: dipentaerythritol

From Table 4, the RBOT life of Hexaester 1 was 100 minutes, the RBOT life of Hexaester 2 was 144 minutes, the RBOT life of Hexaester 3 was 142 minutes, the RBOT life of Hexaester 4 was 251 minutes, and the RBOT life of Hexaester 5 was 312 minutes, and thus Hexaester 1 to Hexaester 5 exhibited excellent oxidation stability. On the other hand, the RBOT life of Hexaester A was 58 minutes, and thus oxidation stability of Hexaester A was not sufficient.

In Test Example 3, Hexaester 1 to Hexaester 5 were not solidified, and the precipitations thereof were not confirmed. It has been seen that Hexaester 1 to Hexaester 5 have excellent oxidation stability and low temperature properties in a well-balanced manner.

Subsequently, an evaluation of the refrigerant oil composition of the present invention was performed through Production Example 4, Examples 6 to 11, Comparative Example 2, Comparative Example 3, and Test Examples 4 to 7.

and Hexaester 1 produced in Example 1 at a weight ratio (Refrigerant Base Oil A:Hexaester 1) of 70:30.

Example 7

Preparation of Refrigerant Oil Composition 2

Refrigerant Oil Composition 2 was prepared by blending Refrigerant Base Oil A produced in Production Example 4 and Hexaester 1 produced in Example 1 at a weight ratio (Refrigerant Base Oil A:Hexaester 1) of 92:8.

Example 8

Preparation of Refrigerant Oil Composition 3

Refrigerant Oil Composition 3 was prepared by blending Refrigerant Base Oil A produced in Production Example 4 and Hexaester 1 produced in Example 1 at a weight ratio (Refrigerant Base Oil A:Hexaester 1) of 96:4.

Example 9

Preparation of Refrigerant Oil Composition 4

Refrigerant Oil Composition 4 was prepared by blending Refrigerant Base Oil A produced in Production Example 4 and Hexaester 1 produced in Example 1 at a weight ratio (Refrigerant Base Oil A:Hexaester 1) of 98:2.

Comparative Example 2

Preparation of Refrigerant Oil Composition 5

Refrigerant Base Oil A produced in Production Example 4 was provided as Refrigerant Oil Composition 5.

Comparative Example 3

Preparation of Refrigerant Oil Composition 6

Refrigerant Oil Composition 6 was prepared by blending Refrigerant Base Oil A produced in Production Example 4 and Hexaester A produced in Comparative Example 1 at a weight ratio (Refrigerant Base Oil A:Hexaester A) of 70:30.

Example 10

Production of Refrigerant Oil Composition 7

Refrigerant Oil Composition 7 was obtained in the same manner as in Comparative Example 1, except that the dipentaerythritol was replaced with a mixture of pentaerythritol (product name: Pentarit-S, manufactured by Koei Chemical Company, Limited) and the bispentaerythritol monoformal produced in Production Example 1, and a molar ratio of the pentaerythritol, the bispentaerythritol monoformal, the 3,5,5-trimethylhexanoic acid, and the 2-ethylhexanoic acid (pentaerythritol/bispentaerythritol monoformal/3,5,5-trimethylhexanoic acid/2-ethylhexanoic acid) was set to 1.00/0.03/2.12/2.68. Refrigerant Oil Composition 7 was subjected to the measurements of NMR and GC, and then it was confirmed that Refrigerant Oil Composition 7 contained hexaester composed of bispentaerythritol monoformal, 3,5,5-trimethylhexanoic acid, and 2-ethylhexanoic acid. Moreover, from the measurement of GC, an area ratio of a peak of the hexaester was 1.89 area %. When the value based on area % was converted into a value based on weight % using a calibration curve method, the value based on weight % was about 1.3 times to about 2.0 times the value based on area %.

Example 11

Production of Refrigerant Oil Composition 8

Refrigerant Oil Composition 8 was obtained in the same manner as in Comparative Example 1, except that the dipentaerythritol was replaced with a mixture of pentaerythritol (product name: Pentarit-S, manufactured by Koei Chemical Company, Limited) and the bispentaerythritol monoformal produced in Production Example 1, the 2-ethylhexanoic acid was replaced with pentanoic acid (manufactured by Tokyo Chemical Industry Co., Ltd.), and a molar ratio of the pentaerythritol, the bispentaerythritol monoformal, the 3,5,5-trimethylhexanoic acid, and the pentanoic acid (pentaerythritol/bispentaerythritol monoformal/3,5,5-trimethylhexanoic acid/pentanoic acid) was set to 1.00/0.03/3.68/1.12. Refrigerant Oil Composition 8 was subjected to the measurements of NMR and GC, and then it was confirmed that Refrigerant Oil Composition 8 contained hexaester composed of bispentaerythritol monoformal, 3,5,5-trimethylhexanoic acid, and pentanoic acid. Moreover, from the measurement of GC, an area ratio of a peak of the hexaester was 2.35 area %. When the value based on area % was converted into a value based on weight % using a calibration curve method, the value based on weight % was about 1.3 times to about 2.0 times the value based on area %.

Test Example 4

Measurement of Kinematic Viscosity of Refrigerant Oil Composition

The kinematic viscosity of Refrigerant Oil Compositions 1 to 8 at 40° C. and 100° C. was measured in accordance with the method of Test Example 1. The results are presented in Tables 5 and 6.

Test Example 5

Evaluation of Oxidation Stability of Refrigerant Oil Composition (Measurement of RBOT Life)

An oxidation stability test was performed on Refrigerant Oil Compositions 1 to 8 in accordance with the method of Test Example 2. The results are presented in Tables 5 and 6. The refrigerant oil composition, which has longer RBOT life, has more excellent oxidation stability.

Test Example 6

Evaluation of Lubricity of Refrigerant Oil Composition (Measurement of Wear Scar Diameter)

A diameter of a wear scar of each of Refrigerant Oil Compositions 1 to 8 was measured by means of a shell four-ball friction tester (manufactured by Shinko Engineering Co., Ltd.). The test was carried out under the conditions where the load was 100 N, the rotating speed was 600 rpm, the duration was 10 minutes, and the temperature was 40° C. (test ball: SUJ-2). After the test, the wear scar diameter was measured. The wear scar diameter was the average value of all of the three stationary balls in both the vertical direction, and horizontal direction. The results are presented in Tables 5 and 6.

Test Example 7

Evaluation of Low Temperature Properties of Refrigerant Oil Composition Containing BZT (BZT Content: 1.5 Weight %) (Confirmation of Presence of Solidification and Precipitation at −20° C.)

(1) Preparation of Refrigerant Oil Composition Containing BZT (BZT Content: 1.5 Weight %)

A refrigerant oil composition composed of Refrigerant Oil Composition 1 and BZT was prepared by blending 2.955 g of Refrigerant Oil Composition 1, and 0.045 g of BZT, followed by heating the mixture at 60° C. In the same manner, refrigerant oil compositions containing Refrigerant Oil Compositions 2 to 8, respectively, and BZT were prepared.

(2) Evaluation of Low Temperature Properties

Each of the refrigerant oil compositions containing Refrigerant Oil Compositions 1 to 8, respectively, and BZT was placed in a glass container by 1 g, and was left to stand for 24 hours in a thermostat container set to −20° C. A case where no solidification or precipitation was confirmed was determined as I, and solidification or precipitation was confirmed was determined as II. The results are presented in Tables 5 and 6.

TABLE 5

|  |  | Refrigerant Oil Composition 1 (Ex. 6) | Refrigerant Oil Composition 2 (Ex. 7) | Refrigerant Oil Composition 3 (Ex. 8) | Refrigerant Oil Composition 4 (Ex. 9) | Refrigerant Oil Composition 5 (Comp. Ex. 2) | Refrigerant Oil Composition 6 (Comp. Ex. 3) |
|---|---|---|---|---|---|---|---|
| Composition (weight ratio) | Refrigerant Base Oil A | 70 | 92 | 96 | 98 | 100 | 70 |
|  | Hexaester 1 | 30 | 8 | 4 | 2 | — | — |
|  | Hexaester A | — | — | — | — | — | 30 |
| Kinematic viscosity (mm²/sec) | 40° C. | 102.1 | 76.3 | 71.6 | 70.7 | 69.0 | 95.0 |
|  | 100° C. | 10.9 | 9.0 | 8.7 | 8.6 | 8.4 | 10.5 |
| RBOT life (min) |  | 109 | 116 | 106 | 121 | 99 | 92 |
| Wear scar diameter (mm) |  | 0.22 | 0.21 | 0.22 | 0.21 | 0.24 | 0.21 |
| Low temperature properties when containing BZT (BZT content: 1.5 wt %) |  | I | I | I | I | II | I |

TABLE 6

|  |  | Refrigerant Oil Composition 7 (Ex. 10) | Refrigerant Oil Composition 8 (Ex. 11) |
|---|---|---|---|
| Kinematic viscosity (mm²/sec) | 40° C. | 69.3 | 69.4 |
|  | 100° C. | 8.4 | 8.9 |
| RBOT life (min) |  | 116 | 563 |
| Wear scar diameter (mm) |  | 0.21 | 0.20 |
| Low temperature properties when containing BZT (BZT content: 1.5 wt %) |  | I | I |

From Tables 5 and 6, the RBOT life of Refrigerant Oil Composition 1 was 109 minutes, the RBOT life of Refrigerant Oil Composition 2 was 116 minutes, the RBOT life of Refrigerant Oil Composition 3 was 106 minutes, the RBOT life of Refrigerant Oil Composition 4 was 121 minutes, the RBOT life of Refrigerant Oil Composition 7 was 116 minutes, and the RBOT life of Refrigerant Oil Composition 8 was 563 minutes, and thus Refrigerant Oil Compositions 1 to 4 and 7 to 8 exhibited excellent oxidation stability compared to Refrigerant Oil Composition 5 and Refrigerant Oil Composition 6. The wear scar diameter of Refrigerant Oil Composition 1 was 0.22 mm, the wear scar diameter of Refrigerant Oil Composition 2 was 0.21 mm, the wear scar diameter of Refrigerant Oil Composition 3 was 0.22 mm, the wear scar diameter of Refrigerant Oil Composition 4 was 0.21 mm, the wear scar diameter of Refrigerant Oil Composition 7 was 0.21 mm, and the wear scar diameter of Refrigerant Oil Composition 8 was 0.20 mm, and thus Refrigerant Oil Compositions 1 to 4 and 7 to 8 exhibited excellent lubricity compared to Refrigerant Oil Composition 5.

Moreover, no solidification or precipitation was observed with Refrigerant Oil Compositions 1 to 4 and 7 to 8 at −20° C., even when each of them contained BZT in an amount of 1.5 weight %, and thus Refrigerant Oil Compositions 1 to 4 and 7 to 8 exhibited excellent low temperature properties when containing BZT, compared to Refrigerant Oil Composition 5. It has been seen from above that Refrigerant Oil Compositions 1 to 4 and 7 to 8, each containing the hexaester of bispentaerythritol monoformal of the present invention, have excellent oxidation stability, lubricity, and low temperature properties when containing BZT, in a well-balanced manner.

INDUSTRIAL APPLICABILITY

The present invention can provide a hexaester of bispentaerythritol monoformal, which has excellent oxidation stability, and a refrigerant oil composition, which contains the hexaester of bispentaerythritol monoformal, has excellent characteristics, such as oxidation stability, lubricity, and low temperature properties.

The invention claimed is:

1. Hexaester of bispentaerythritol monoformal, which is mixed ester of bispentaerythritol monoformal represented by the following formula (I), and carboxylic acids:

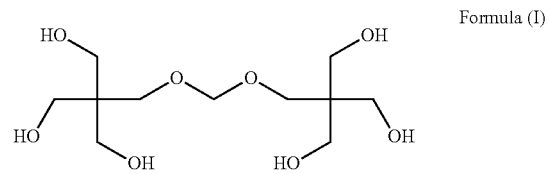

Formula (I)

wherein the carboxylic acids comprise C9 branched aliphatic monocarboxylic acid, and any one of carboxylic acids selected from C4 to C8 aliphatic monocarboxylic acids.

2. The hexaester of bispentaerythritol monoformal according to claim 1, wherein the C9 branched aliphatic monocarboxylic acid is 3,5,5-trimethylhexanoic acid.

3. A refrigerant oil composition, comprising:
hexaester of bispentaerythritol monoformal,
wherein the hexaester of bispentaerythritol monoformal is mixed ester of bispentaerythritol monoformal represented by the following formula (I), and carboxylic acids:

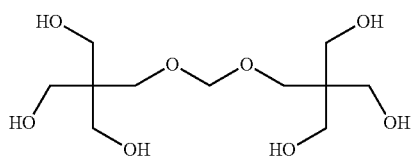

Formula (I)

wherein the carboxylic acids comprise C9 branched aliphatic monocarboxylic acid, and any one of carboxylic acids selected from C4 to C8 aliphatic monocarboxylic acids.

4. A working fluid composition for refrigerator, comprising:
a refrigerant oil composition; and
a refrigerant,
wherein the refrigerant oil composition comprises hexaester of bispentaerythritol monoformal,
wherein the hexaester of bispentaerythritol monoformal is mixed ester of bispentaerythritol monoformal represented by the following formula (I), and carboxylic acid:

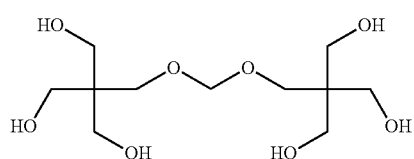

Formula (I)

wherein the carboxylic acids comprise C9 branched aliphatic monocarboxylic acid, and any one of carboxylic acids selected from C4 to C8 aliphatic monocarboxylic acids.

* * * * *